United States Patent [19]

Wong

[11] Patent Number: 4,616,998
[45] Date of Patent: Oct. 14, 1986

[54] FACE BOW AND METHOD OF USE IN ORTHODONTIC PROCEDURES

[76] Inventor: Brian W. Wong, 215 Red Rock Way #J106, San Francisco, Calif. 94131

[21] Appl. No.: 650,283
[22] Filed: Sep. 12, 1984
[51] Int. Cl.$^4$ ............................................. A61C 19/04
[52] U.S. Cl. ......................................... 433/73; 33/514
[58] Field of Search ....................... 433/68, 69, 72, 73, 433/75; 33/174 D

[56] References Cited

U.S. PATENT DOCUMENTS

| | | | |
|---|---|---|---|
| 2,648,130 | 8/1953 | Avery | 433/73 |
| 2,794,253 | 6/1957 | Fitzsimmons | 433/69 |
| 2,806,284 | 9/1957 | Stuart | 433/69 |
| 3,213,541 | 10/1965 | Raffman | 33/174 D |
| 3,218,716 | 11/1965 | Stuart | 433/73 |
| 3,224,096 | 12/1965 | Stuart | 433/56 |
| 4,234,307 | 11/1980 | Draheim | 433/73 |
| 4,328,620 | 5/1982 | Mack et al. | 33/174 D |

FOREIGN PATENT DOCUMENTS 2012800 10/1971 Fed. Rep. of Germany ... 33/174 D

Primary Examiner—John J. Wilson
Attorney, Agent, or Firm—Fitch, Even, Tabin & Flannery

[57] ABSTRACT

A novel face bow and method of its use for accurately transferring gnathological relationship data from a patient to an articulator, the face bow including radioluscent arm pieces with radiopaque markers or indicators for locating critical points, the method of use comprising the mounting of the face bow on a patient in generally conventional fashion and then producing a cephalometric head x-ray of the patient with the improved face bow in place, the radioluscent arm pieces permitting anatomical features of the patient to be clearly viewed with precise correlation to reference planes. Radiopaque markers are located at various selected points on the face bow to accurately reflect the position of points of interest, such as an articulator's axis of rotation, such that these points become superimposed with the patient's anatomical features on the cephalometric head film.

10 Claims, 4 Drawing Figures

FACE BOW AND METHOD OF USE IN ORTHODONTIC PROCEDURES

The present invention relates to a novel improved face bow and method of its use in dental and orthodontic procedures for accurately transferring gnathological relationship data to an articulator and cephalometric head films and more particularly to an arbitrary improved face bow as defined below and its method of use.

BACKGROUND OF THE INVENTION

In numerous dental and orthodontic procedures, casts are made of the teeth of both the upper and lower jaws of a patient. These dental casts are then mounted on an articulator to reproduce the location and movement of the lower teeth and mandible relative to the upper jaw and maxillary teeth. Various methods of reproducing the teeth for the upper and lower jaws of patients and mounting them in gnathological articulators have been commonly employed in the prior art for a number of purposes, including the making of artificial dentures, gnathological positioners, etc. The importance of using instruments such as articulators is to approximate as closely as possible the patient's opening and closing axis of rotation or arc of closure of the jaws.

It is sufficient in terms of the present invention to understand that the position of patient's teeth in the upper and lower jaws and the relative positioning of the upper and lower jaws must be precisely reproduced in an articulator in order to permit the dentist or orthodontist to determine and carry out the corrective measures which are required for a given patient.

Face bows are commonly used in the prior art for transferring maxillary relationship data from patients to such articulators. See, e.g., U.S. Pat. No. 3,218,716 to Stuart. Present arbitrary face bows are used for recording and relating the patient's jaws and dentition to a universal reference plane and point (ideally the axis-orbital plane) oriented relative to the patient's head. These references serve an essential function in properly orienting and transferring spatial information to the dental casts on the articulator.

The face bow is the mechanical means by which data is transferred from the patient to the articulator and the dental casts mounted thereupon. The spatial orientation of the patient's dentition and jaws as well as the spatial orientation of the dental casts mounted on the articulator are correlated with each other by the references described above through the use of the face bow. The primary purpose for the face bow and the techniques involving the use of the face bow is to locate, transfer and reproduce as accurately as possible the patient's exact jaw location and movements on the articulator. Only in this way can the patient's dynamic occlusion be reproduced and studied. Prior art face bows have performed this function by establishing approximately the orientation of the patient's dental casts relative to a universal reference plane and axis. The face bow is then mechanically fitted onto the articulator to enable a dental cast of the maxillary teeth to be precisely mounted in the articulator. Subsequent transfer of additional dental casts from the patient to the articulator is also enabled using this technique without redetermining the articulator settings for each transfer.

Certain prior art face bows are of the "kinematic" type, and were designed to locate an opening and closing axis for the lower jaw or mandible. This axis can be described as the center of rotation about which the mandible moves at least during the first third of its opening movement (without translation) when the condyles are seated in the fossae.

In an effort to streamline upon the above-noted kinematic technique, "estimated" or "arbitrary" techniques evolved where the exact hinge axis or "true axis" for the mandible was estimated from various facial landmarks. The external auditory meatus (or ear hole) has become one of the most popular facial landmarks for locating the face bow. Accordingly, face bows which are located upon the patient's head by means of the auditory meatus are also commonly referred to as "ear bows" as well as "arbitrary", "estimated" or "anatomical" face bows.

A typical application for such an arbitrary face bow involves the initial preparation of accurate upper and lower dental casts of the patient's teeth. An interocclusal record of the patient's bite relationship is also taken, most commonly in softened wax. There are many different interocclusal bite relationships possible for a given patient. The most traditional and reproducible relationship is the specific jaw relationship commonly referred to as "centric relation". The wax record provides the information necessary to correctly orient the lower cast of the patient relative to the upper cast. The upper cast in turn is related by the arbitrary face bow to the universal reference plane on the patient's head. The arbitrary face bow mechanically records this relationship by using convenient features or facial landmarks of the patient. Currently, in addition to the external auditory meatus or ear hole as noted above, most arbitrary face bows employ the depression at the nasion or bridge of the nose in order to establish the necessary reference plane.

The position of the arbitrary face bow on the patient's head may be described by means of various reference planes which are well known in the prior art. Physical or mechanical conversion factors are commonly provided on the face bow so that the position of the arbitrary face bow on the patient's head approximates these reference planes.

One exemplary reference plane that was used was defined to exist between the tragus of the ear and the corner of the eye. Since this reference plane depended upon strictly facial landmarks, it could not be correlated with the skeletal structure of the patient, the reproducible mounting of the articulator, nor with a lateral cephalometric head film of the patient.

Accordingly, palpation reference landmarks were established to more closely approximate skeletal structures of the patient. An example of such a reference plane involved palpation or location by touch of the condyle and the lower rim of the bony orbit. However, it was found that palpation of the condyle is only a rough approximation of the patient's true axis.

The most sophisticated and reproducible reference plane is the "axis-orbital" reference plane. This reference plane involves location of the exact true axis so that it can be precisely correlated to articulators. In addition to the exact true axis, this reference plane is also located with respect to the lower rim of the orbit, by means of palpation or touch. This reference plane has not been correlated in the prior art to either cephalometric landmarks nor to facial landmarks in relation to the arbitrary face bow. However, the arbitrary face bow has been designed on the assumption that the face bow most nearly approximates the axis orbital plane. As described below, it has been found that this assumption is not correct and, that, as a result, prior art face bows fail to provide precise correlation between these various reference planes and an articulator.

Radiographs or head x-rays in the form of orthodontic cephalometric head films are also commonly used in an attempt to accurately correlate various reference planes to diagnostic instruments. This is because of their ability to clearly illustrate the relationship between various anatomical features of the patient. A variety of orthodontic reference planes in the form of cephalometric analyses are established from such head films, one of the most popular being the Frankfort Horizontal reference plane. This plane is located by means of the "Porion" (the external auditory meatus of the ear) and the "Orbitale" (the lower rim of the orbit). However, it has been found that this reference plane also often fails to correlate with various facial landmarks and with the articulator.

In other cephalometric analyses, various anatomical features of the patient are analyzed by means of angular and linear relationships established between the various anatomical features and reference planes of the patient. Again it has been found that there still remains a need for correlation of the lateral cephalometric head film analysis to the other various diagnostic instrumentation.

In general, in order to more accurately reproduce, diagnose and create a treatment plan for a given patient, it is necessary for the orthodontist to more precisely correlate one or more of these reference planes with various diagnostic instruments such as the articulator, referred to above, and to lateral cephalometric head films. Such a precise correlation, however, is not readily possible with existing techniques.

In any event, it is believed clearly apparent that dentists and orthodontists practice different variations of these techniques in diagnosing and treating patients. In practically all such existing techniques, the dentist and orthodontist now rely substantially on experience. Accordingly, there has been found to remain a need for a method and apparatus permitting more accurate transfer of data relating the patient to the lateral cephalometric head films or the like and to gnathological instruments such as the articulator. Accordingly, the present invention provides a means for more accurately reproducing spatial information and for correlating this information directly from the patient's reference planes, the patient's lateral cephalometric head film and to an articulator.

SUMMARY OF THE INVENTION

It is therefore an object of the invention to provide an improved method in dental practice for more accurately obtaining and transferring gnathological or maxillary relationship data from a patient to an articulator or the like by means of an arbitrary face bow.

It is a more particular object of the invention to provide a method of the type referred to above wherein the arbitrary face bow is positioned on the patient, and a cephalometric x-ray head film is then taken of the patient with the arbitrary face bow in place, in order to enable precise cephalometric head film analysis of various anatomical features of the patient in accurate correlation with an articulator.

It is a related object of the invention to provide an improved arbitrary face bow to facilitate practice of the method of the invention as summarized above, the improved arbitrary face bow being of a type that includes conventional means for accurately and reproducibly locating the face bow on the head of the patient, and that further includes radioluscent arm pieces and at least one radiopaque plug for locating certain critical points to be displayed on the lateral cephalometric head film, the radioluscent arm pieces permitting anatomical features of the patient to be clearly viewed with precise reference to the instrument axis as determined by the radiopaque plug.

Presently, the improved face bow is of a type commonly referred to as an estimated or arbitrary face bow and includes mounting means for accurately and reproducibly locating the improved face bow upon the patient's head with respect to the external auditory meati or ear holes and the depression at nasion or bridge of the nose. The improved face bow is further defined to include transfer means for positioning the improved face bow relative to a cephalostat and to an articulator for transferring data from the improved face bow and the articulator. With such an arrangement, the radiopaque marker is preferably positioned on the face bow in order to permit more accurate transfer of data from the cephalometric head film to the articulator.

Additional objects and advantages of the invention are made apparent in the following description having reference to the accompanying drawings.

DESCRIPTION OF THE PREFERRED EMBODIMENT

Figure 1:
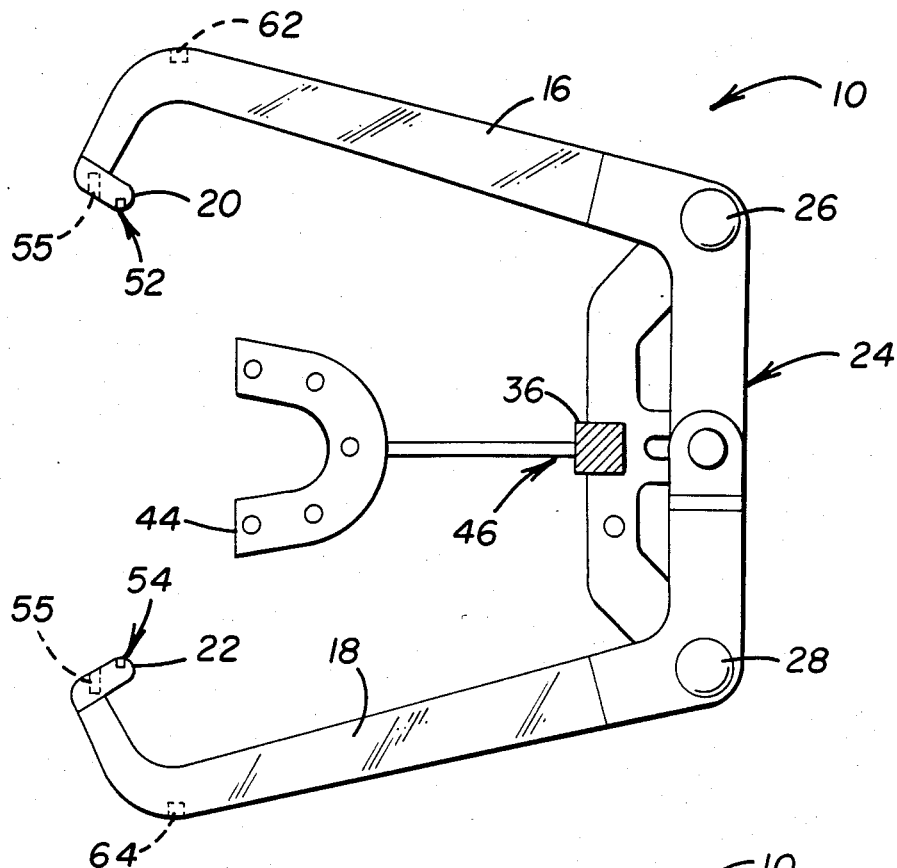
FIG. 1 is a plan view of an improved arbitrary face bow constructed in accordance with the present invention.

As mentioned above, conventional arbitrary or estimated face bows are commonly employed for obtaining gnathological or maxillary relationship data from a patient. It will be apparent from the following description that the present invention may also be employed in connection with face bows of other types and its method of use in that regard will also be apparent.

Generally, the conventional arbitrary face bow is positioned upon the patient relative to selected anatomical features of the patient's head or face in order to assure that the face bow is always positioned in substantially the same relationship to the patient. In accordance with conventional practice, the arbitrary face bow is formed with transfer means for reproducing maxillary and mandibular relationship data from the patient on an articulator. Additional data may conventionally be obtained in conjunction with a cephalometric head x-ray of the patient as described above. Such a head x-ray is generally indicated at 12 in FIG. 3. More particularly, analytical data derived for generally conventional orthodontic procedures may be developed upon a transparency of the type represented in FIG. 4, the transparency of FIG. 4 being derived from a head x-ray such as that indicated in FIG. 3. In any event, prior art orthodontic procedures have required the orthodontist to exercise particular skill and judgement in interpolating data derived from the transparency 14 to the patient, and to the articulator. This was necessary because precise correlation between analysis data such as that derived from the transparency 14 was not available with respect to either the conventional face bow or the articulator.

By contrast, as will be made more apparent in the following description, the present invention provides an improved face bow and method for using this improved face bow to accurately obtain gnathological relationship data from a patient whereby the data obtained by means of the improved face bow is accurately and precisely oriented with respect to selected anatomical features of the patient's head. This permits the orthodontist to develop additional data, for example, by means of various analytical techniques and to combine that data with information obtained, for example, from the face bow in a gnathological instrument such as an articulator.

This capability of the invention is made possible by mounting of the improved face bow upon the patient's head in generally conventional fashion for obtaining selected gnathological relationship data. With the improved face bow in place upon the patient's head, a normal standardized cephalometric head x-ray is then produced with the additional purpose of accurately orienting various instrumental and anatomical features of the patient.

Preferably, the improved face bow is formed with radioluscent lateral arm pieces which will appear as lightly shaded areas in the head x-ray. In this manner, the position of the face bow is clearly observable relative to the various anatomical features of the patient's head. However, because of the radioluscent character of the arm pieces, all of the anatomical features of the patient's head are clearly illustrated within the head x-ray. At the same time, the improved face bow is also formed with one or more radiopaque indicators positioned in various precise locations such that the radiopaque indicators are clearly indicated within the head x-ray as reference points. In accordance with this summary of the invention, the construction of the improved face bow as well as its method of use for accurately obtaining gnathological relationship data from a patient is described in greater detail below.

Figure 2:
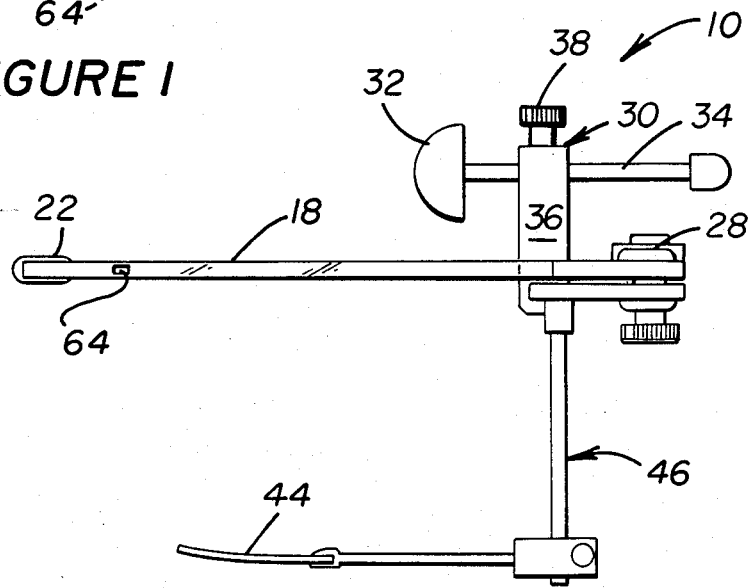
FIG. 2 is a side view of the improved arbitrary face bow of FIG. 1.

Referring in combination to FIGS. 1 and 2, shown is an arbitrary face bow 10 that includes both conventional features and features according to the present invention. The conventional features of face bow 10 include lateral arm pieces 16 and 18. When the face bow is properly positioned upon a patient's head, the lateral arm pieces 16 and 18 extend along the sides of the patient's head so that ear plugs 20 and 22 mounted at the rearward ends of the arm pieces 16 and 18 can be positioned within the external auditory meati or ear holes for locating the face bow upon the patient's head. In accordance with past conventional practice, the ear plugs 20 and 22 project inwardly and forwardly to facilitate accurate and reproducible placement of the ear plugs within the ear holes.

The forward ends of arm pieces 16 and 18 are interconnected with a compound cross-member 24 by means of pivot connections 26 and 28. In this manner, the arm pieces can be pivoted for proper positioning of the ear plugs 20 and 22 within the ear holes of the patient.

Referring particularly to FIG. 2, a glabella support device 30 is adjustably arranged upon the cross-member 24 for positioning the face bow relative to the depression at nasion notch of the patient and establishing a fixed planar relationship between the face bow and the patient's head. For this purpose, the support device 30 includes a locating pad 32 shaped to fit into the nasion notch of the patient. The locating pad 32 is mounted upon a shaft 34 which is slideable through a housing 36 of the support device 30 in order to permit the locating pad 32 to be moved into stable engagement with the nasion notch of the patient. With the above described forward projection of ear plugs 20 and 22, the opposing pressure of the locating pad 32 against the nasion notch of the patient ensures a stable and reproducible placement of the face bow 10 on the patient. Once the locating pad 32 is properly positioned upon the patient, it is locked in place by means of a screw 38. The support device 30 is omitted from the face bow as illustrated in FIG. 1 in order to better illustrate other components of the face bow.

Figure 3:
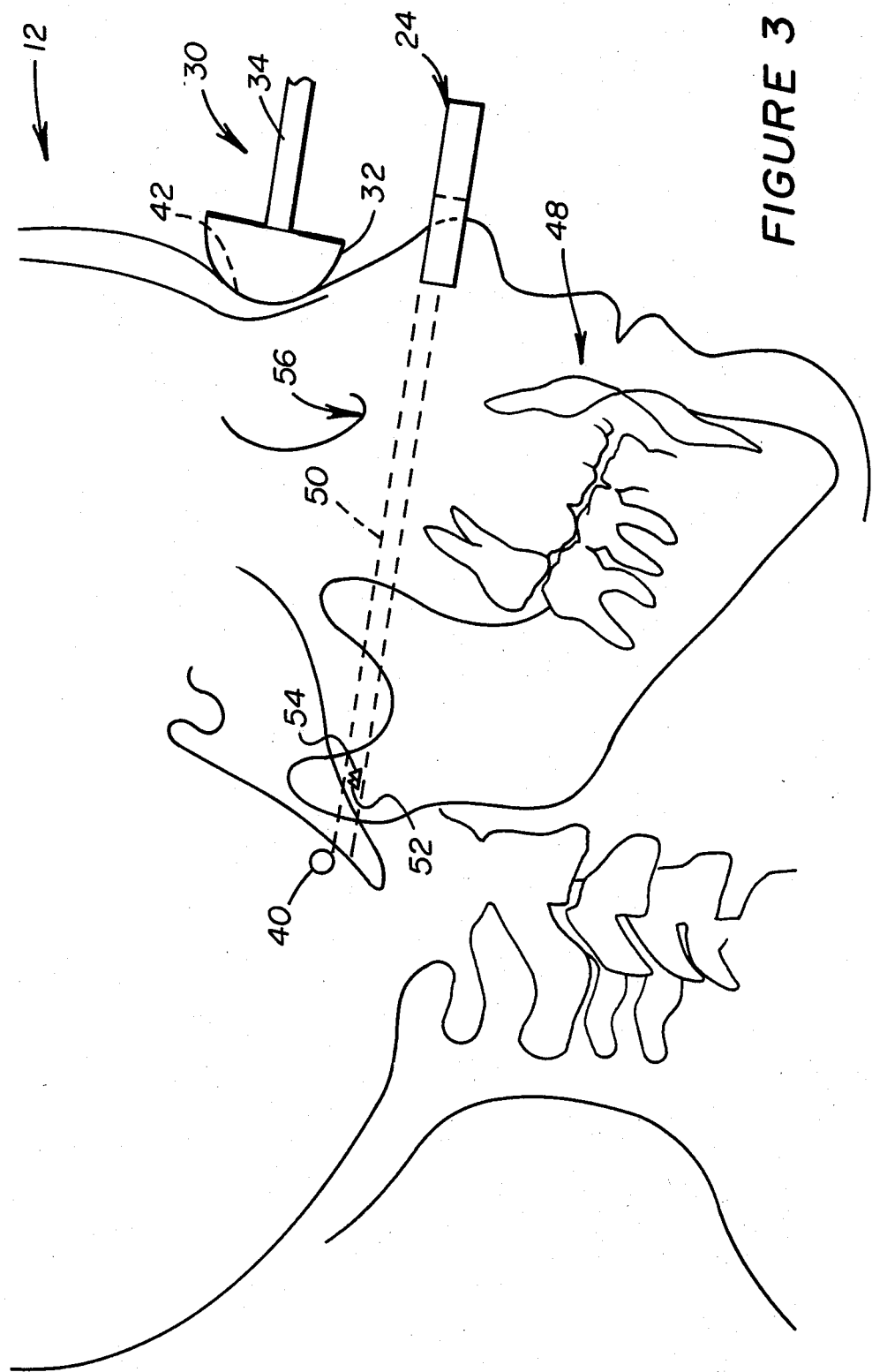
FIG. 3 is a representation of a cephalometric head x-ray taken of a patient with the improved arbitrary face bow of the present invention positioned on the patient's head.

Conventional positioning of the face bow relative to the patient's head may be better seen with reference to FIG. 3. An auditory meatus of the patient is generally indicated at 40. Similarly, the nasion notch of the patient is generally indicated at 42 with the locating pad 32 being shown in proper position relative to the patient's head. With the face bow being located by means of the external auditory meati 40 and the nasion notch 42, the face bow is in a predetermined planar arrangement upon the patient's head which can be accurately reproduced so that data can be taken from the patient in this manner at different times with the face bow being in substantially the same orientation relative to the patient's head each time.

Referring again to FIGS. 1 and 2, an impression transfer device 44 is centrally mounted on the face bow below the arm pieces 16 and 18 by means of a transfer fork shaft assembly 46 so that the impression device 44 may be engaged with the dentition 48 of the patient (see FIG. 3).

The preceding components of the face bow are substantially in accordance with the prior art. In order to adapt the face bow according to the present invention, the lateral arm pieces 16 and 18 are preferably formed from a radioluscent material, preferably a plastic, such that they will produce only a shadow as illustrated at 50 in a head x-ray film as shown in FIG. 3. In this manner, the location of the arm pieces and accordingly the plane of a face bow may be observed by viewing the head x-ray film with the radioluscent character of the arm pieces permitting the anatomical features of the patient underlying the arm pieces to be clearly visible in the head x-ray.

In addition, one or more radiopaque indicators such as those indicated at 52 and 54 are mounted upon the improved face bow so that they will be clearly visible in the head x-ray in order to permit accurate correlation of various instrument characteristics and data on the head x-ray or a derivation thereof. Preferably, the two indicators 52 and 54 are located on the ear plugs of the improved face bow corresponding to a critical feature of the articulator, namely its axis of rotation, in order to better facilitate transfer of data between the head x-ray or a derivation thereof and the articulator. As shown in FIGS. 1 and 2, the radiopaque indicators 52 and 54 are metallic inserts embedded within the translucent ear plugs 20 and 22.

Additional or alternate locations for radiopaque indicators in the face bow are also possible in addition to those indicated at 52 and 54. For example, similar indicators or metallic inserts could be arranged along the arm pieces 16 and 18. In this regard, the estimated axis is arbitrarily assumed to correspond with the patient's actual axis when the face bow is positioned on the patient's head. It has been common practice in the prior art to assume that the estimated axis location is a fixed distance forward of the external auditory meatis of the patient. Accordingly, with the improved face bow design illustrated in FIG. 1, the estimated axis for the patient could be located on each of the arm pieces 16 and 18 a predetermined distance forward along the length thereof with respect to each ear plug 20 and 22. Since the forward tips of the ear plugs 20 and 22 are intended to rest within the external auditory meati of the patient, this estimated axis is also intended to provide a reproducible reference point with respect to the face bow. In any event, such radiopaque indicators could be mounted in one or more locations upon the improved face bow.

Finally, with respect to the radiopaque indicators 52 and 54, it may be seen in FIG. 3 that they are in substantially overlapping relationship. Accordingly, it might be possible in some applications to employ only one such indicator on the improved face bow. However, since there may be some asymmetries between the left and right ear holes of the patient, the separate indicators 52 and 54 are preferably mounted on each of the arm pieces to provide greater accuracy.

Also shown in FIG. 1 are two indents or depressions 62 and 64 in respective arm pieces 16 and 18. These indents are positioned to provide means for positioning a patient's head in a cephalostat without adding more than a minimal outside force which could cause the face bow according to the present invention to move or shift in position from its desired position while the cephalometric head film is being taken.

The face bow 10 is designed to be mounted in a conventional manner directly on an articulator (not shown) of conventional construction for transferring patient data to the articulator. Small holes 55 formed in each of the ear plugs 20 and 22 mount on pins of the articulator, the cross-member 24 also interacting with the articulator to establish a predetermined and reproducible planar relationship between the face bow and articulator. Thus, the ear plug holes 55 and cross-member 24 serve as transfer means for positioning the face bow relative to the articulator.

The method of use for a face bow according to the present invention is believed clearly apparent from the preceding description. However, the method of the invention is summarized below in order to assure a complete understanding of the invention.

With the improved face bow 10 positioned upon the patient's head as illustrated in the x-ray of FIG. 3, the location of the cross-member 24 is shown in addition to components of the support device 30. The arm pieces 16 and 18 appear as a shadow represented by the broken lines 50. Furthermore, the radiopaque indicators 52 and 54 are clearly visible in order to permit accurate correlation as described above.

Once the face bow 10 is positioned in the manner described above, a head x-ray such as that illustrated in FIG. 3 is taken of the patient's head to illustrate various anatomical features as well as the components of the improved face bow described immediately above. In addition to the dentition of the patient as generally indicated at 48, the auditory meati 40 and the nasion notch 42, other anatomical features of the patient which are shown by the head x-ray include the anatomic orbitale 56 which is also an important reference point in many orthodontic analysis techniques.

Figure 4:
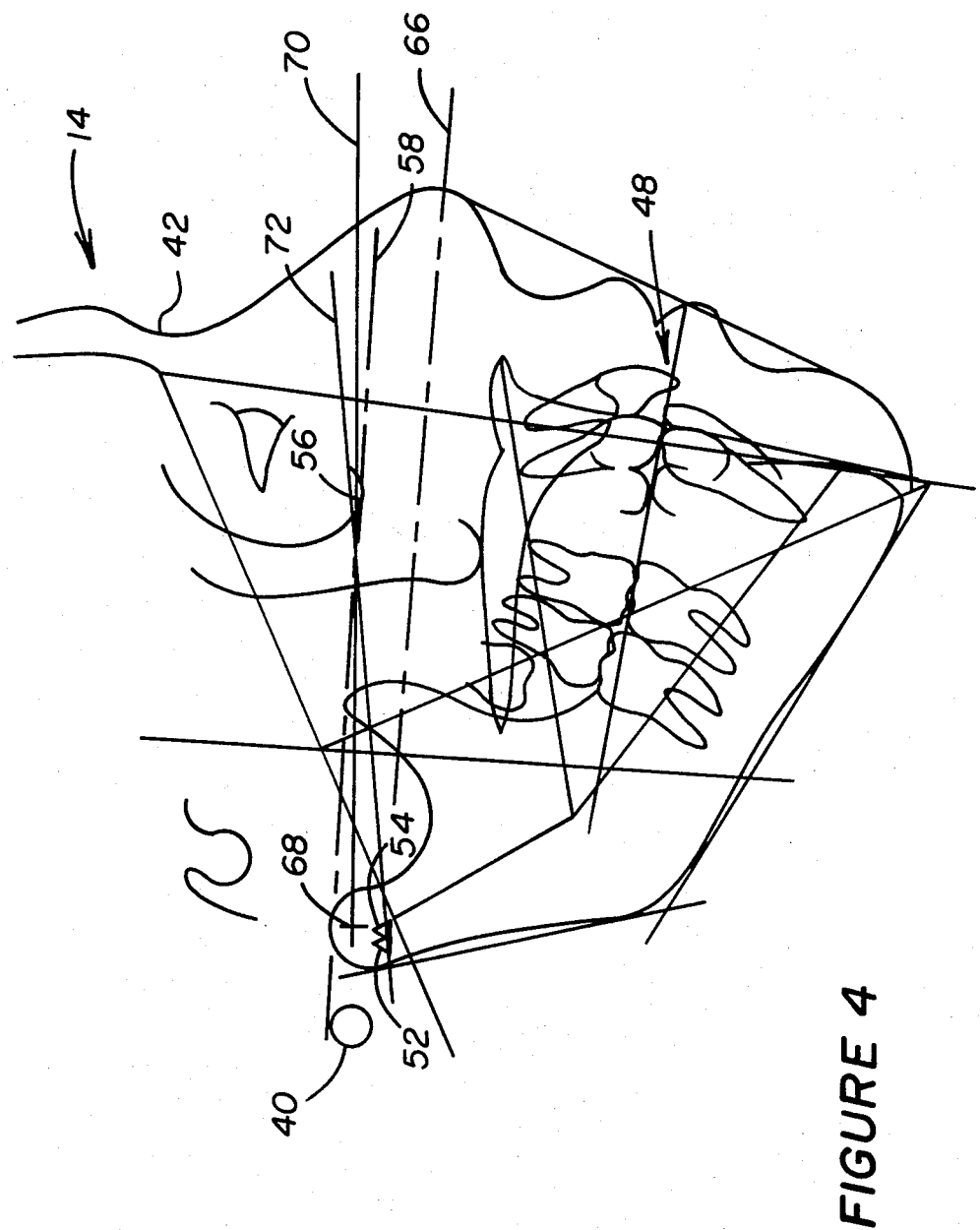
FIG. 4 is a representation of a generally conventional orthodontic cephalometric analysis technique (Rickett's) applied to a representation of a patient's anatomical features taken from a head x-ray of the type illustrated in FIG. 3.

Generally, FIG. 4 is derived from a head x-ray such as that illustrated in FIG. 3 representing a condition of "centric occlusion". In particular, referring to FIG. 4, the line 58 joining the top of the external auditory meati or ear hole 40 and the bottom of the anatomic orbitale 56 is referred to as the "Frankfort plane", a common reference for many orthodontic analysis techniques. The various lines shown in the analysis of FIG. 4 in addition to the Frankfort plane 58 are typical of such an analysis and represent in particular a technique referred to as "Rickett's analysis". The line 66 represents the indicated plane of the face bow. The probable true axis of rotation is shown at 68 and thus the axis orbital plane is shown at 70. Since the estimated axis orbital plane developed by the hinge axis points 52,54 and the orbitale point 56 shown at 72 is displaced from the true axis-orbital plane 70, it can be seen that the present invention provides a method and means for modifying a patient's treatment in light of this data.

With the transparency analysis illustrated in FIG. 4 being derived from a head x-ray such as that illustrated in FIG. 3, both the instrument axis represented by the radiopaque indicators 52 and 54 as well as the plane of the improved face bow, as indicated at 66 in FIG. 4, may be accurately and reproducibly correlated with other maxillary relationship data derived from the analysis of FIG. 4. Accordingly, this data may also be very precisely transferred to the articulator in order to facilitate and permit greater accuracy in the work of occlusion.

Numerous variations both in connection with the improved face bow and its method of use as disclosed above are believed apparent. For example, the radioluscent and radiopaque components of the arbitrary face bow 10 can also be employed on other types and shapes of face bows. At the same time, data obtained from the face bow and from analysis techniques such as that illustrated in FIG. 4 may also be transferred or applied to other gnathological instruments or devices in addition to the conventional articulator referred to in connection with the face bow 10. Different imaging techniques other than the use of x-ray film and transparencies is also envisioned, e.g., the use of digital computer assisted imaging techniques in cephalometric x-ray imaging and analysis. Accordingly, the scope of the present invention is defined only by the following appended claims.

What is claimed is:

1. A method for accurately obtaining gnathological relationship data from a patient, the steps comprising:
    forming a radioluscent face bow having lateral arm pieces formed from radioluscent material selected for permitting anatomical features of the patient to be clearly viewed in a cephalometric head film;
    positioning a radiopaque marker on said radioluscent face bow in a position to enable accurate detection of said marker in a cephalometric head film;
    mounting said radioluscent face bow upon the patient's head in a predetermined position relative to selected external anatomical features of the patient;

obtaining one or more dentition impressions of the patient by means of the radioluscent face bow; and producing a cephalometric head film of the patient with the radioluscent face bow in place on the patient in order to enable accurate correlation between anatomical features of the patient and said radiopaque marker on said radioluscent face bow.

2. The method of claim 1 further comprising the step of mounting the radioluscent face bow on an articulator so as to accurately transfer thereto the gnathological relationship data of the patient and whereby gnathological relationship data taken from said cephalometric head film can also be accurately transferred to the articulator.

3. The method of claim 2 wherein said step of positioned a radiopaque marker includes the step of positioning at least one radiopaque marker in a position corresponding to the hinge axis of said articulator when the radiolucent face bow is mounted thereon, such that said marker defines and locates this axis on the cephalometric head film in relation to anatomical landmarks shown thereon.

4. The method of claim 3 wherein the radioluscent face bow is of an arbitrary type including a radioluscent ear plug attached to each said lateral arm pieces and including means for locating said radiolucent face bow relative to the patient's nasal depression, wherein the step of positioning a radiopaque marker further includes the step of positioning a radiopaque marker in each said ear plug such that said ear plug radioopaque markes identify where said radiolucent face bow is mounted on an articulator.

5. The method of claim 1 wherein the radioluscent face bow is of an arbitrary type including means for accurately and reproducibly locating the radioluscent face bow upon the patient's head relative to the patient's external auditory meati and nasal depression.

6. In a face bow of a type adapted for interaction with an articulator for transferring gnathological relationship data to the articulator, the articulator having an axis of movement, and of the type including lateral components adapted for arrangement alongside the patient's head in order to mount the face bow thereupon, the face bow including additional means for mounting the face bow upon the patient's head in a predetermined position relative to selected external anatomical features, the improvement comprising the lateral components of the face bow being formed from radioluscent material in order to permit underlying anatomical features of the patient to be clearly illustrated in a cephalometric x-ray image taken of the patient's head with the face bow in place, a first radiopaque indicator mounted upon the face bow in accordance with a predetermined characteristic of the face bow for accurate detection of said indicator in a cephalometric x-ray machine, said radiopaque indicator formed on the face bow in correlation with the axis of rotation movement for the articulator, and wherein said face bow is of an arbitrary type wherein the lateral components are arm pieces including a radioluscent ear plug in each arm piece for positioning in the external auditory meati of the patient, and wherein a second radiopaque indicator is mounted on one of said earplugs and a third radiopaque indicator is mounted on the other of said earplugs.

7. The face bow of claim 6 wherein said second and third radiopaque indicators are metallic inserts disposed in the translucent ear plugs.

8. In a face bow of the type including lateral components adapted for arrangement alongside the patient's head in order to mount the face bow thereupon, the face bow including additional means for mounting the face bow upon the patient's head in a predetermined position relative to selected external anatomical features, the improvement comprising the lateral components of the face bow being formed from radioluscent material in order to permit underlying anatomical features of the patient to be clearly illustrated in a cephalometric x-ray image taken of the patient's head with the face bow in place, at least one radiopaque indicator mounted upon the face bow in accordance with a predetermined characteristic of the face bow for accurate detection of said indicator in a cephalometric x-ray machine, and means for aligning said face bow in said cephalometric x-ray machine such that said face bow fits into said machine and enables the face bow and the head of the patient to be positioned to enable conventional orientation of said face bow.

9. In a face bow of the type including lateral components adapted for arrangement alongside the patient's head in order to mount the face bow thereupon, the face bow including additional means for mounting the face bow upon the patient's head in a predetermined position relative to selected external anatomical features, the improvement comprising the lateral components of the face bow being formed from radioluscent material in order to permit underlying anatomical features of the patient to be clearly illustrated in a cephalometric x-ray image taken of the patient's head with the face bow in place, and at least one radiopaque indicator mounted upon the face bow in accordance with a predetermined characteristic of the face bow for accurate detection of said indicator in a cephalometric x-ray machine, and wherein said face bow's lateral components define indents formed in a predetermined position thereon to assist in lining up the patient's head and face bow in the cephalometric x-ray machine such that conventional positioning means in a cephalometric x-ray machine will have minimum effect on the position of said face bow with respect to the patient's head.

10. A method for accurately obtaining gnathological relationship data from a patient, the steps comprising:

forming a radiolucent face bow shaped so as to permit anatomical features of the patient to be clearly viewed in a cephalometric x-ray image;

positioning a radiopaque marker on said radioluscent face bow in a position to enable accurate detection of said marker in a cephalometric x-ray image;

mounting said radioluscent face bow upon the patient's head in a predetermined position relative to selected external anatomical features of the patient;

obtaining one or more dentition impressions of the patient by means of the radioluscent face bow; and producing a cephalometric x-ray image of the patient with the radioluscent face bow in place on the patient in order to enable accurate correlation between anatomical features of the patient and said radiopaque marker on said radioluscent face bow.

* * * * *